United States Patent [19]

Kogan et al.

[11] Patent Number: 5,622,937
[45] Date of Patent: Apr. 22, 1997

[54] COMPOSITIONS AND METHODS OF INHIBITING THE BINDING OF E-SELECTIN OR P-SELECTIN OR SIALYL-LEWIS$^x$ OR SIALYL-LEWIS$^A$

[75] Inventors: Timothy P. Kogan, Sugar Land; Brian Dupre, Houston; Huong Dao, Houston; Pamela J. Beck, Houston, all of Tex.

[73] Assignee: Texas Biotechnology Corporation, Houston, Tex.

[21] Appl. No.: 641,341

[22] Filed: May 1, 1996

Related U.S. Application Data

[63] Continuation of Ser. No. 236,517, Apr. 29, 1994, abandoned.
[51] Int. Cl.$^6$ .............................. A61K 31/70; C07H 15/00
[52] U.S. Cl. .............................. 514/25; 536/4.1; 536/17.2; 536/18.4
[58] Field of Search .............................. 514/25; 536/4.1, 536/17.2, 18.4

[56] References Cited

U.S. PATENT DOCUMENTS

| | | | |
|---|---|---|---|
| 5,211,937 | 5/1993 | Brandley et al. | 424/1.73 |
| 5,212,298 | 5/1993 | Rademacher et al. | 536/55.2 |
| 5,268,364 | 12/1993 | Kojima et al. | 514/25 |
| 5,280,113 | 1/1994 | Rademacher et al. | 536/55.2 |
| 5,304,640 | 4/1994 | Lasky et al. | 536/23.5 |
| 5,318,890 | 6/1994 | Rosen et al. | 435/7.24 |

OTHER PUBLICATIONS

Needham et al. *Proc. Natl. Acad. Sci.* 1993, 90, 1359–1363.
Green et al. *Biochem. Biophys. Res. Commun.* 1992, 188(1), 244–251.
Springer *Nature* 1990, 346, 425–434.

*Primary Examiner*—Gary L. Kunz
*Assistant Examiner*—Kathleen Kahler Fonda
*Attorney, Agent, or Firm*—Dressler, Goldsmith, Milnamow & Katz, Ltd.

[57] ABSTRACT

This invention relates to compounds that inhibit the binding of E-selectin or P-selectin to sialyl-Lewis$^x$ or sialyl-Lewis$^a$ presented on a cell surface having the general structure:

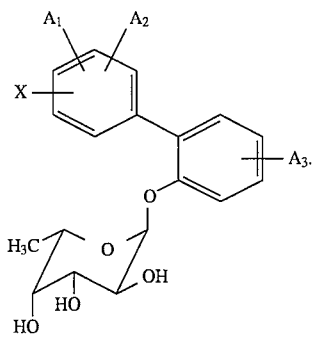

This invention also relates to methods of inhibiting the binding of E-selectin or P-selectin to sialyl-Lewis$^x$ or sialyl-Lewis$^a$ presented on a cell surface using said compounds and to pharmaceutically active compositions comprising compounds that inhibit the binding of E-selectin to sialyl-Lewis$^x$ and to methods of treatment of septic shock, ARDS, Crohn's disease, chronic inflammatory diseases, such as psoriasis and rheumatoid arthritis, and reperfusion injuries that occurs following heart attacks, strokes and organ transplants and to the treatment of cancer.

6 Claims, No Drawings

COMPOSITIONS AND METHODS OF INHIBITING THE BINDING OF E-SELECTIN OR P-SELECTIN OR SIALYL-LEWIS$^x$ OR SIALYL-LEWIS$^A$

This is a continuation of application Ser. No. 08/236,517, filed Apr. 29, 1994, now abandoned.

This invention relates to compounds that inhibit the binding of E- or P-selectin to sialyl-Lewis$^x$ and sialyl-Lewis$^a$ and to methods of inhibiting the binding of E- or P-selectin to sialyl-Lewis$^x$ or sialyl-Lewis$^a$ using said compounds. This invention also relates to pharmaceutically active compositions comprising compounds that inhibit the binding of E- or P-selectin to sialyl-Lewis$^x$ or sialyl-Lewis$^a$.

BACKGROUND OF THE INVENTION

E-selectin, which has also been called ELAM-1 for endothelial leukocyte adhesion molecule-1 and LECAM-2 for lectin cell adhesion molecule, is a glycoprotein that is found on the surface of endothelial cells, the cells that line the interior wall of capillaries. E-selectin recognizes and binds to the carbohydrate sialyl-Lewis$^x$ (sLe$^x$), which is present on the surface of certain white blood cells. E-selectin helps white blood cells recognize and adhere to the capillary wall in areas where the tissue surrounding the capillary has been infected or damaged. E-selectin is actually one of three selectins now known. The other two are L-selectin and P-selectin. P-selectin is expressed on inflamed endothelium and platelets, and has much structural similarity to E-selectin and can also recognize sialyl-Lewis$^x$. The structure of sialyl-Lewis$^x$ and sialyl-Lewis$^a$ (sLe$^a$) are shown in formulas I$_a$ and I$_b$ below:

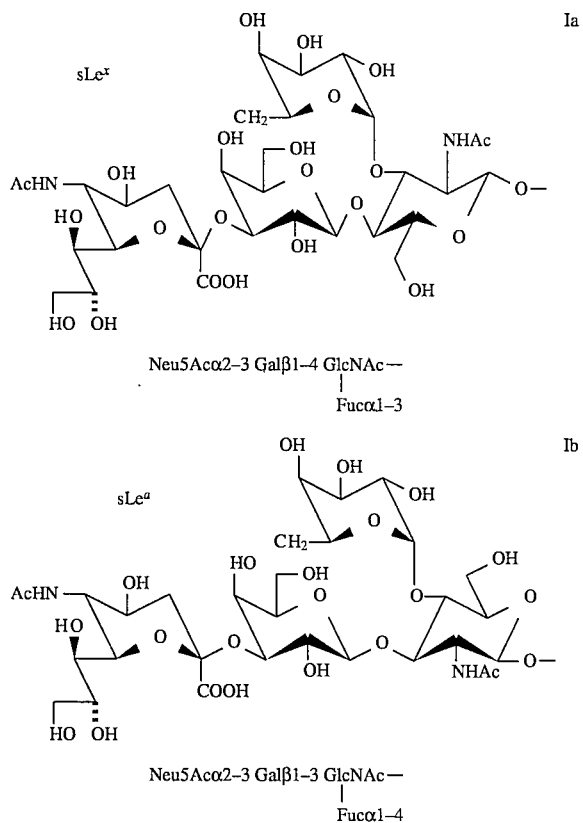

When a tissue has been invaded by a microorganism or has been damaged, white blood cells, also called leukocytes, play a major role in the inflammatory response. One of the most important aspects of the inflammatory response involves the cell adhesion event. Generally, white blood cells are found circulating through the bloodstream. However, when a tissue is infected or becomes damaged, the white blood cells must be able to recognize the invaded or damaged tissue and be able to bind to the wall of the capillary near the affected tissue and diffuse through the capillary into the affected tissue. E-selectin helps two particular types of white blood cells recognize the affected sites and bind to the capillary wall so that these white blood cells may diffuse into the affected tissue.

There are three main types of white blood cells: granulocytes, monocytes and lymphocytes. Of these categories, E-selectin recognizes sLe$^x$ presented as a glycoprotein or glycolipid on the surface of monocytes and neutrophils. Neutrophils are a subclass of granulocytes that phagocytose and destroy small organisms, especially bacteria. Monocytes, after leaving the bloodstream through the wall of a capillary, mature into macrophages that phagocytose and digest invading microorganisms, foreign bodies and senescent cells.

Monocytes and neutrophils are able to recognize the site where tissue has been damaged by binding to E-selectin, which is produced on the surface of the endothelial cells lining capillaries when the tissue surrounding a capillary has been infected or damaged. Typically, the production of E- and P-selectins are increased when the tissue adjacent a capillary is affected. P-selectin is present constitutively in storage granules from which it can be rapidly mobilized to the cell surface after the endothelium has been activated. In contrast, E-selectin requires de novo RNA and protein synthesis, and peak expression does not occur until about 4–6 hours after activation, and declines to basal levels after about 24–48 hours. White blood cells recognize affected areas because sLe$^x$ moieties present on the surface of the white blood cells bind to E- and P-selectin. This binding slows the flow of white blood cells through the bloodstream, since it mediates the rolling of leukocytes along the activated endothelium prior to integrin mediated attachment and migration, and helps to localize white blood cells in areas of injury or infection.

While white blood cell migration to the site of injury helps fight infection and destroy foreign material, in many instances this migration can get out of control, with white blood cells flooding to the scene, causing widespread tissue damage. Compounds capable of blocking this process, therefore, may be beneficial as therapeutic agents. Thus, it would be useful to develop inhibitors that would prevent the binding of white blood cells to E- or P-selectin. For example, some of the diseases that might be treated by the inhibition of selectin binding to sLe$^x$ include, but are not limited to, ARDS, Crohn's disease, septic shock, traumatic shock, multi-organ failure, autoimmune diseases, asthma, inflammatory bowel disease, psoriasis, rheumatoid arthritis and reperfusion injury that occurs following heart attacks, strokes and organ transplants. In addition to being found on some white blood cells, sLe$^a$, a closely related regiochemical isomer of sLe$^x$, is found on various cancer cells, including lung and colon cancer cells. It has been suggested that cell adhesion involving sLe$^a$ may be involved in the metastasis of certain cancers and that inhibitors of sLe$^a$ binding may be useful in the treatment of some forms of cancer.

SUMMARY OF THE INVENTION

The present invention provides compounds having the structure of formula II below:

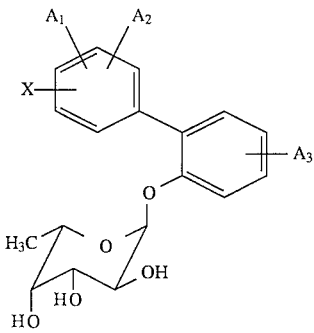

(II)

wherein X is selected from the group consisting of —$CO_2R$, —$(CH_2)_nO(CH_2)_mCO_2R$, —$(CH_2)_nCO_2R$, —$O(CH_2)_nCO_2R$, —$CONH(CHR_2)_nCO_2R$, —$(CH_2)_nSO_3H$, —$(CH_2)_nPO_3D_1D_2$, and —OH;

$A_1$ and $A_2$ are independently selected from the group consisting of hydrogen, halogen, lower alkyl, —OR, —$(CH_2)_nNR(CH_2)_mCO_2R$, —NRR, —CN, —$N_3$, and —$NO_2$; and $A_3$ is hydrogen, halogen, lower alkyl, —$(CH_2)_pNH_2$, —$(CH_2)_pNR(CH_2)_qCO_2R$, or —$(CH_2)_pNH(CH_2)_qCH_3$;

where n and m are independently 1 to 6, p and q are independently 0 to 12, R is lower alkyl or hydrogen, $R_2$ is any functional group that can be derived from an available α or β amino acid, and $D_1$ and $D_2$ are independently hydrogen or methyl, and the pharmaceutically acceptable salts, esters, amides and prodrugs thereof.

More particularly, this invention provides compounds of the formula III.

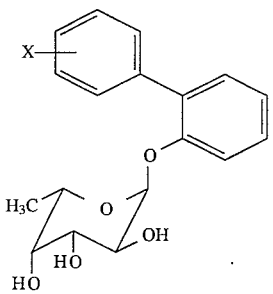

III wherein X is —$CO_2R$ or —$(CH_2)_nO(CH_2)_mCO_2R$, where n and m are independently 1 to 6 inclusive and R is hydrogen or lower alkyl, and the pharmaceutically acceptable salts, esters, amides and prodrugs thereof.

The present invention also provides a method of inhibiting the binding of E- or P-selectin to sLe$^x$ or sLe$^a$ comprising the step of administering to a patient an effective amount of a compound having the structure of formula II or III to inhibit the binding of E- or P-selectin to sLe$^x$ or sLe$^a$, and a pharmaceutically active composition comprising a compound of formula II or III and a pharmaceutically acceptable carrier.

Also provided is a method for treating diseases such as ARDS, Crohn's disease, septic shock, traumatic shock, multi-organ failure, autoimmune diseases, asthma, inflammatory bowel disease, psoriasis, rheumatoid arthritis, reperfusion injury that occurs following heart attacks, strokes and organ transplants and cancer, which comprises administering to a patient in need of such treatment a therapeutically effective amount of a compound having the formula II or III to reduce the symptoms of the disease.

DETAILED DESCRIPTION OF THE PREFERRED EMBODIMENTS

It has been found that compounds having the formula (II) shown below act to inhibit E- or P-selectin binding to sLe$^x$ or sLe$^a$:

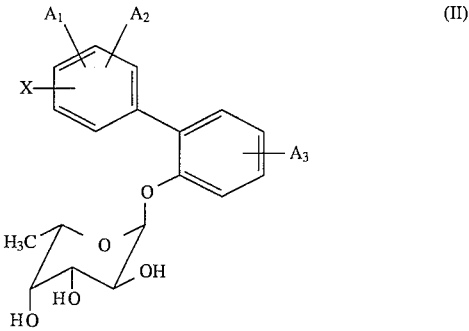

(II)

wherein X is selected from the group consisting of —$CO_2R$, —$(CH_2)_nO(CH_2)_mCO_2R$, —$(CH_2)_nCO_2R$, —$O(CH_2)_nCO_2R$, —$CONH(CHR_2)_nCO_2R$, —$(CH_2)_nSO_3H$, —$(CH_2)_nPO_3D_1D_2$, and —OH;

$A_1$ and $A_2$ are independently selected from the group consisting of hydrogen, halogen, lower alkyl, —OR, —$(CH_2)_nNR(CH_2)_mCO_2R$, —NRR, —CN, —$N_3$, and —$NO_2$; and $A_3$ is hydrogen, halogen, lower alkyl, —$(CH_2)_pNH_2$, —$(CH_2)_pNR(CH_2)_qCO_2R$, or —$(CH_2)_pNH(CH_2)_qCH_3$;

where n and m are independently 1 to 6, p and q are independently 0 to 12, R is lower alkyl or hydrogen, $R_2$ is any functional group that can be derived from an available α or β amino acid, and $D_1$ and $D_2$ are independently hydrogen or methyl, and the pharmaceutically acceptable salts, esters, amides and prodrugs thereof.

The most preferred compounds of the present invention have the formula III below:

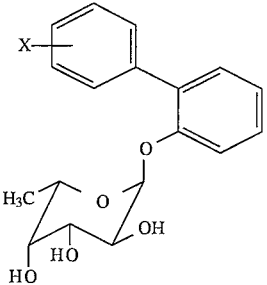

wherein X is —$CO_2R$ or —$(CH_2)_nO(CH_2)_mCO_2R$, where n and m are independently 1 to 6 inclusive and R is hydrogen or lower alkyl, and the pharmaceutically acceptable salts, esters, amides and prodrugs thereof.

As used herein, the term "alkyl" shall mean a monovalent straight chain or branched chain group of 1 to 12 carbon atoms including, but not limited to, methyl, ethyl, n-propyl, isopropyl, n-butyl, sec-butyl, isobutyl, tert-butyl and the like.

The term "lower alkyl" shall mean any alkyl group having from one to six carbon atoms.

The term "halogen" shall mean any atom selected from the group consisting of chlorine, fluorine, bromine, and iodine.

The term "pharmaceutically acceptable salts, esters, amides and prodrugs" as used herein refers to those carboxylate salts, amino acid addition salts, esters, amides and prodrugs of the compounds of the present invention which are, within the scope of sound medical judgement, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of the compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmirate, stearate, laurate, borate, benzoate, lactate, phosphate, tosylate, citrate, maleate, fumarate, succinate, tartrate, naphthylate, mesylate, glucoheptonate, lactiobionate, laurylsulphonate salts and the like. These may include cations based on the alkali and alkaline earth metals, such as sodium, lithium, potassium, calcium, magnesium and the like, as well as nontoxic ammonium, quaternary ammonium and amine cations including, but not limited to, ammonium, tetramethylammonium, tetraethylammonium, methylamine, dimethylamine, trimethylamine, triethylamine, ethylamine, and the like. (See, for example S. M. Berge, et al., "Pharmaceutical Salts," *J. Pharm. Sci.*, 66:1–19 (1977), which is incorporated herein by reference.)

Examples of pharmaceutically acceptable, nontoxic esters of the compounds of this invention include $C_1$ to $C_6$ alkyl esters wherein the alkyl group is a straight or branched chain. Acceptable esters also include $C_5$ to $C_7$ cycloalkyl esters as well arylalkyl esters such as, but not limited to benzyl. $C_1$ to $C_4$ alkyl esters are preferred. Esters of the compounds of the present invention may be prepared according to conventional methods.

Examples of pharmaceutically acceptable, nontoxic amides of compounds of this invention include amides derived from ammonia, primary $C_1$ to $C_6$ alkyl amines and secondary $C_1$ to $C_6$ dialkyl amines wherein the alkyl groups are straight or branched chain. In the case of secondary amines the amine may also be in the form of a 5 or 6 membered heterocycle containing one nitrogen atom. Amides derived from ammonia, $C_1$ to $C_3$ alkyl primary amides and $C_1$ to $C_2$ dialkyl secondary amides are preferred. Amides of the compounds of the invention may be prepared according to conventional methods.

The term "prodrug" refers to compounds that are rapidly transformed in vivo to yield to the parent compound of the above formula, for example by hydrolysis in blood. A thorough discussion is provided in T. Higuchi and V. Stella, "Pro-drugs as Novel Delivery Systems", Vol 14 of the A.C.S. Symposium Series, and in Bioreversible Carriers in Drug Design, ed. Edward B. Roche, American Pharmaceutical Association and Pergamon Press, 1987, both of which are incorporated herein by reference.

The present invention also provides for pharmaceutically active compositions and methods of treatment that utilize the compounds of the present invention. It is also contemplated that pharmaceutically active compositions may contain a compound of the present invention and other compounds that inhibit or compete with E or P-selectin binding to $sLe^x$ or $sLe^a$, including $sLe^x$ and $sLe^a$ themselves.

As used herein, the term "patient" can include both humans and other animals.

The pharmaceutical compositions of the present invention may include one or more of the compounds having the above structures II or III formulated together with one or more nontoxic, physiologically acceptable carriers, adjuvants or vehicles, which are collectively referred to herein as carriers, for parenteral injection, for oral administration in solid or liquid form, for rectal or topical administration and the like.

The compositions can be administered to humans and animals either orally, rectally, parentally (intravenously, intramuscularly, or subcutaneously), intracisternally, intravaginally, intraperitoneally, locally (powders, ointments or drops), or as buccal or nasal sprays.

Compositions suitable for parenteral injection may comprise physiologically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyol, (propylene glycol, polyethylene glycol, glycerol and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispersing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monostearate and gelatin.

If desired, and for more effective distribution, the compounds can be incorporated into slow or timed release or targeted delivery systems such as polymer matrices, liposomes, and microspheres. They may be sterilized, for example, by filtration through a bacteria-retaining filter, or by incorporating sterilizing agents in the form of sterile water, or some other sterile injectable medium immediately before use.

Solid dosage forms for oral administration include capsules, tablets, pills, powders and granules. In such solid dosage forms, the active compound or a pro-drug ester is admixed with at least one inert customary excipient (or carrier) such as sodium citrate or dicalcium phosphate or (a) fillers or extenders, as for example, starches, lactose, sucrose, glucose, mannitol and silicic acid, (b) binders, as for example, carboxymethylcellulose, alginates, gelatin, polyvinylpyrrolidone, sucrose and acacia, (c) humectants, as for example, glycerol, (d) diintegrating agents, as for example, agar-agar, calcium carbonate, potato or tapioca starch, alginic acid, certain complex silicates and sodium carbonate, (e) solution retarders, as for example, paraffin, (f) absorption accelerators, as for example, quaternary ammonium compounds, (g) wetting agents, as for example, cetyl alcohol and glycerol monostearate, (h) adsorbents, as for example, kaolin and bentonite, and (i) lubricants, as for example, talc, calcium stearate, magnesium stearate, solid polyethylene glycols, sodium lauryl sulfate or mixtures thereof. In the case of capsules, tablets and pills, the dosage forms may also comprise buffering agents.

Solid compositions of a similar type may also be employed as fillers in soft and hard-filled gelatin capsules using such excipients as lactose or milk sugar as well as high molecular weight polyethylene glycols and the like.

Solid dosage forms such as tablets, dragees, capsules, pills and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions that can be used are polymeric substances and waxes.

The active compounds can also be in microencapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil and sesame seed oil, glycerol, tetrahydrofurfuryl alcohol, polyethylene glycols and fatty acid esters of sorbitan or mixtures of these substances, and the like.

Besides such inert diluents, the compositions can also include adjuvants, such as wetting agents, emulsifying and suspending agents, sweetening, flavoring and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth or mixtures of these substances and the like.

Compositions for rectal administrations are preferably suppositories, which can be prepared by mixing the compounds of the present invention with suitable nonirritating excipients or carriers such as cocoa butter, polyethylene glycol or a suppository wax, which are solid at ordinary temperatures but liquid at body temperature and therefore melt in the rectal or vaginal cavity and release the active component.

Dosage forms for topical administration of a compound of this invention include ointments, powders, sprays and inhalants.

The active component is admixed under sterile conditions with a physiologically acceptable carrier and any needed preservatives, buffers or propellants as may be required. Ophthalmic formulations, eye ointments, powders and solutions are also contemplated as being within the scope of this invention.

The compounds of this invention can also be administered in the form of liposomes. As is known in the art, liposomes are generally derived from phospholipds or other lipid substances. Liposomes are formed by mono or multilamellar hydrated liquid crystals that are dispersed in an aqueous medium. Any nontoxic, physiologically acceptable and metabolizable lipid capable of forming liposomes can be used. The present compositions in liposome form can contain, in addition to the selectin binding inhibitors of the present invention, stabilizers, preservatives, excipients and the like. The preferred lipids are the phospholipids and the phosphatidyl cholines (lecithins), both natural and synthetic. Methods to form liposomes are well known in the art.

Actual dosage levels of active ingredient in the compositions of the present invention may be varied so as to obtain an amount of active ingredient that is effective to obtain the desired therapeutic response for a particular composition and method of administration. The selected dosage levels, therefore, depends on the desired therapeutic effect, on the route of administration, on the desired duration of treatment and other factors.

The total daily dosage of the compounds of this invention administered to a host in single or divided doses may be in the range of from about 5 mg to about 250 mg per kilogram of body weight. Dosage unit compositions may contain such submultiples thereof as may be used to make up the daily dosage. It will be understood, however, that the specific dose level for any particular patient, whether human or other animal, will depend upon a variety of factors including the body weight, general health, sex, diet, time and route of administration, rates of absorption and excretion, combination with other drugs and the severity of the particular disease being treated.

In particular, the compounds of the present invention may be used to treat a variety of diseases relating to inflammation and cell-cell recognition and adhesion. For example, the compounds of the present invention may be administered to a patient to treat septic shock, chronic inflammatory diseases such as psoriasis and rheumatoid arthritis, and reperfusion tissue injury that occurs following heat attacks, strokes and organ transplants, traumatic shock, multi-organ failure, autoimmune diseases, asthma and inflammatory bowel disease. In each case, an effective amount of the compounds of the present invention is administered either alone or as part of a pharmaceutically active composition to a patient in need of such treatment. It is also recognized that a combination of the compounds may be administered to a patient in need of such administration. The compounds of the present invention may also be administered to treat other diseases that are associated with cell-cell adhesion. As the present compounds inhibit the binding of E- or P-selectin with $sLe^x$ or $sLe^a$, any disease that is related to this interaction may potentially be treated by the inhibition of this binding interaction.

In addition to being found on some white blood cells, $sLe^a$ is found on various cancer cells, including lung and colon cancer cells. It has been suggested that cell adhesion involving $sLe^a$ may be involved in the metastasis of certain cancers and that inhibitors of $sLe^a$ binding might be useful in the treatment of some forms of cancer.

Many of the compounds of the present invention may be synthesized according to the general synthetic scheme shown in schemes 1 and 2 where $A_1$, $A_2$ and $A_3$ are defined above:

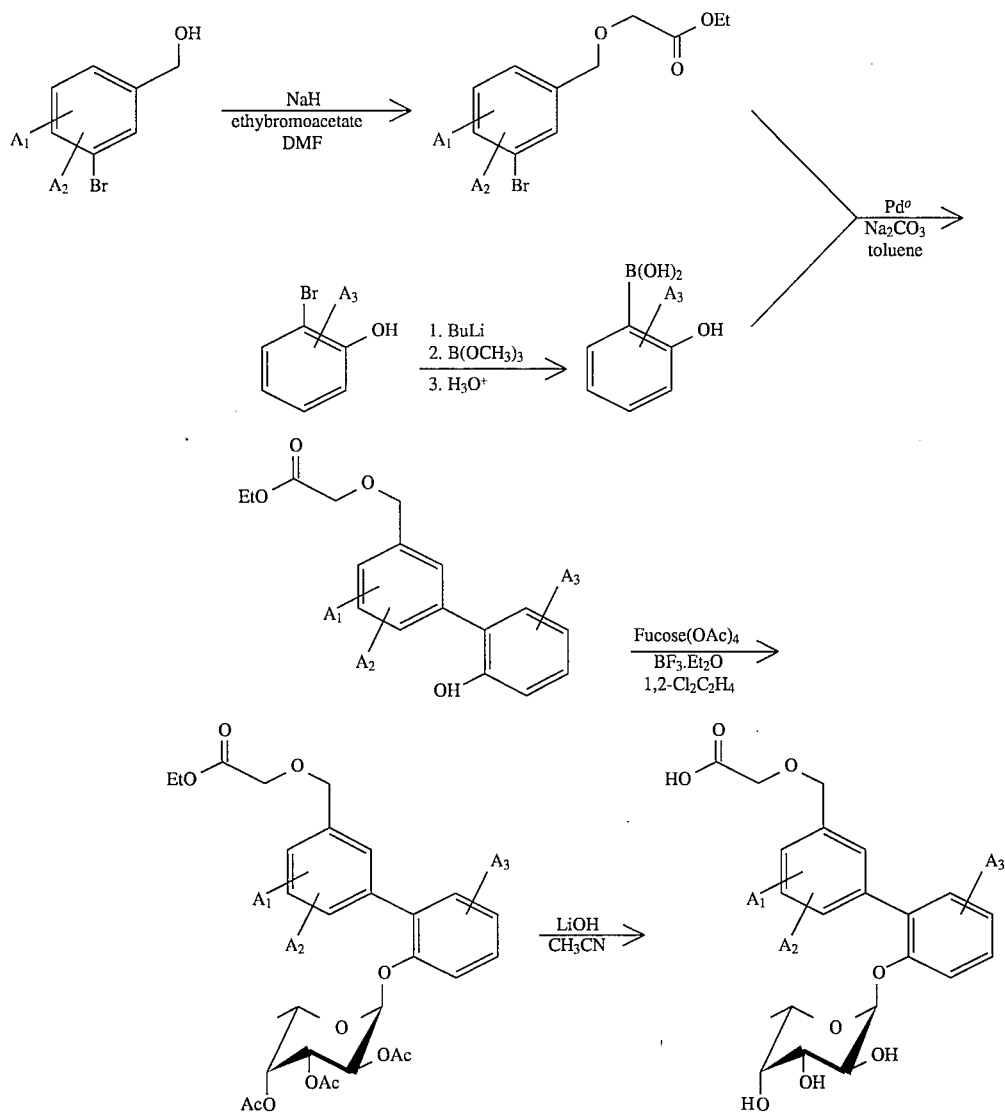
Scheme 1
In this scheme, the biphenyl ester is constructed using a palladium (O) catalyzed coupling of a substituted hydroxyphenyl boronic acid and a bromoaryl ester. The resulting phenol is glycosylated by treatment with fucopyranose tetraacetate and boron trifluoride etherate, and subsequent hydrolysis provides the compound of the present invention.

Scheme 2

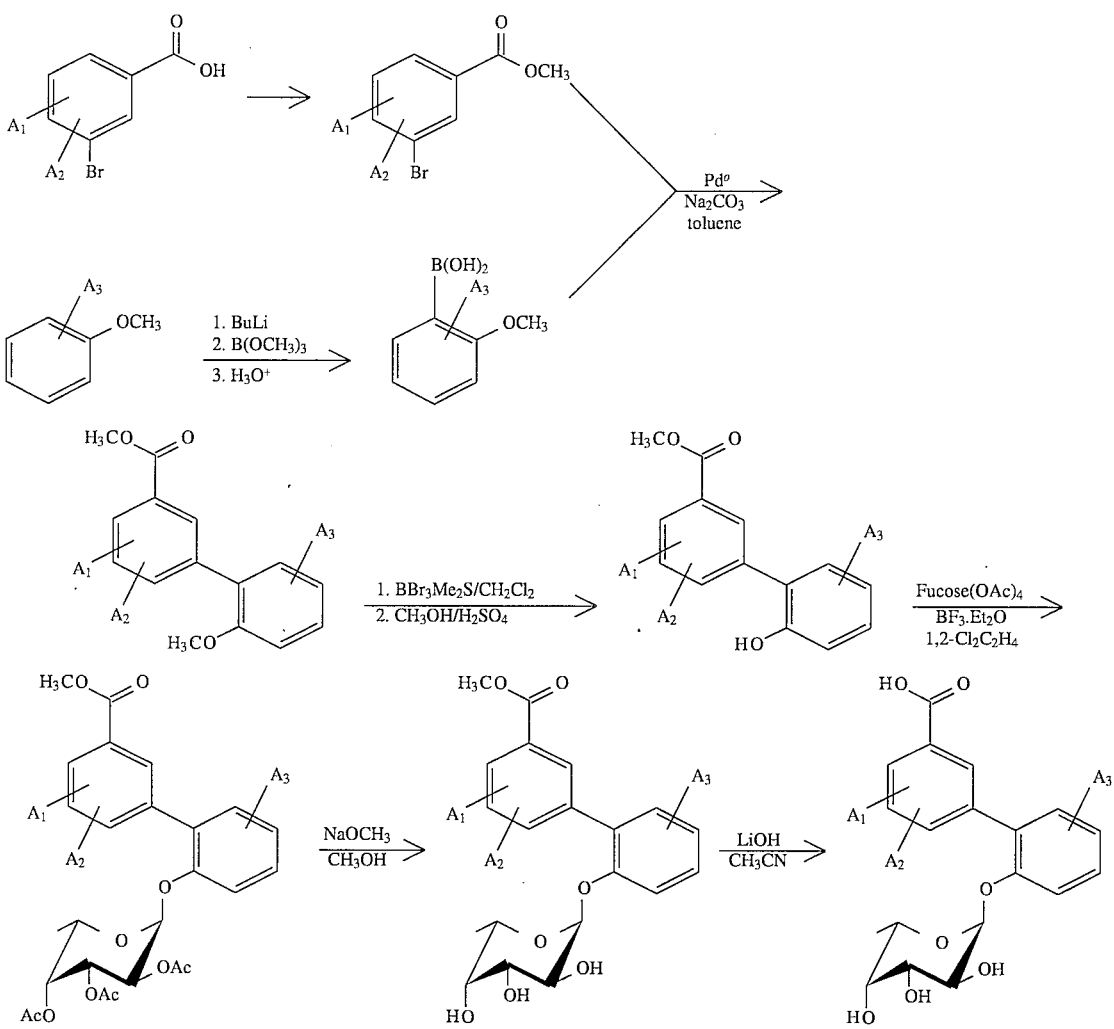

In this reaction scheme, a substituted phenylbenzoic ester is coupled with an aryl boronic acid in the presence of a palladium catalyst and base to give a biphenyl compound. The phenol is deprotected with tribromide dimethyl sulfide, then the phenol functionality is reacted with a protected fucopyranoside in the presence of boron trifluoride etherate. The desired compound is obtained by treatment with base to hydrolyze the esters.

The present invention may be illustrated by the following representative, non-limiting examples.

EXAMPLE 1

3-(2-(α-L-Fucopyranosyloxy)phenyl)benzyloxyacetic Acid

Part A: 3-Bromobenzyl alcohol (2.0 g) was dissolved in dimethyl formamide (50 ml) in a dry 100 ml flask under nitrogen. Sodium hydride (0.5 g of a 60% suspension in mineral oil, washed with hexane, 11.8 mmol) was added in portions and the mixture was stirred for one hour at room temperature. Ethyl bromoacetate (1.2 ml, 11.8 mmol) was added drop-wise and the reaction was stirred overnight at room temperature then mixed with water (150 ml) and extracted with methylene chloride (3×20 ml). The extracts were combined, washed with water (50 ml), saturated sodium chloride solution (50 ml) and then dried (MgSO$_4$). The solution was filtered and concentrated and the residue was purified by flash chromatography (SiO$_2$, gradient hexane to ethyl acetate) which gave 2.35 g (80%) of ethyl 3-bromobenzyloxyacetate as an oil.

Part B: 2-Bromophenol (10.0 g, 57.8 mmol) was dissolved in dry THF (100 ml) in a dry 250 ml flask flushed with nitrogen. The mixture was chilled in a dry ice/2-propanol bath, n-butyl lithium (51 ml of a 2.5M solution in hexanes, 127.2 mmol) was added then the cooling bath was exchanged for an ice-water bath. The reaction was stirred for an hour at 0° C. then trimethyl borate (6.9 ml, 60.7 mmol) was added to the slurry which became homogeneous after a few minutes. The mixture was stirred at room temperature overnight then treated with 2N aqueous HCl to pH 3, mixed well for 30 minutes and extracted with ether (3×25 ml). The organic materials were combined, dried (MgSO$_4$) then concentrated under reduced pressure which gave 7.6 g (91%) of 2-hydroxybenzeneboronic acid as a white solid, m.p. 156°–158° C.

Ethyl 3-bromobenzyloxyacetate (2.28 g, 8.35 mmol), 2-hydroxybenzeneboronic acid (2.52 g, 18.3 mmol), tetrakis(triphenylphosphine)palladium(O) (170 mg), sodium carbonate (1.3 g, 12 mmol) in water (4 ml) and toluene (40 ml)

was degassed under nitrogen in a 100 ml flask fitted with a reflux condenser. The mixture was heated at reflux overnight then mixed with 2N HCl to pH 6, and extracted with ethyl acetate. The organic materials were separated, dried (MgSO$_4$) then concentrated under reduced pressure. The residue was purified by flash chromatography (SiO$_2$, gradient hexane to 3:1 hexane/ethyl acetate) which provided 0.89 g (37%) of ethyl (3-(2-hydroxyphenyl)benzyloxy) acetate.

Part C: Ethyl 3-(2-hydroxyphenyl)benzyloxyacetate (0.85 g, 2.97 mmol) was dissolved in 1,2-dichloroethane (25 ml) in a dry 50 ml flask. L-Fucose tetraacetate (1.97 g, 5.94 mmol) was added in one portion, then boron trifluoride etherate (1.86 ml, 14.84 mmol) was added slowly. The mixture was stirred under nitrogen overnight at room temperature then mixed with water (50 ml). The organic material was separated and the aqueous portion was extracted with dichloromethane (3×5 ml). The extracts were combined with the original organic fraction, dried (MgSO$_4$) then concentrated under reduced pressure. The residue was purified by flash chromatography (SiO$_2$, gradient elution hexane to 3:1 hexane/ethyl acetate) which provided 1.0 g (61%) of ethyl 3-(2-(2,3,4-tri-O acetyl-$\alpha$-L-fucopyranosyloxy)phenyl)benzyloxyacetate.

Part D: Ethyl 3-(2-(2,3,4-tri-O-acetyl-$\alpha$-L-fucopyranosyloxy)phenyl)benzyloxyacetate (0.97 g, 1.74 mmol) was dissolved in acetonitrile (10 ml) in a 25 ml flask, and treated with a solution of potassium hydroxide (0.41 g, 7.3 mmol) in water (5 ml) and the mixture was stirred at room temperature overnight. An additional 0.16 g potassium hydroxide was added and the mixture was stirred for 18 hours then acidified to pH 5.5 with concentrated hydrochloric acid. The mixture was concentrated under reduced pressure and the residue was purified by HPLC (reverse-phase, gradient elution 5–50% acetonitrile in water, 0.1% trifluoroacetic acid, monitored at 254 nm) which gave 0.14 g (20%) of 3-(2-(2-L-fucopyranosyloxy)phenyl)benzyloxyacetic acid m.p. 68°–69° C.; $^1$H NMR (300 MHz DMSO-d$_6$): 7.02–7.62 (comp, 8H), 5.49 (s, 1H), 4.59 (s, 2H), 4.09 (s, 2H), 3.30–3.80 (comp, 7H plus H$_2$O), 0.93 (d, J=4, 3H); IR (KBr): 3431, 2938, 1731, 1217, 1080, 1038, 1018, 964, 846, 755; analysis: calculated for C$_{21}$H$_{24}$O$_8$.0.3[CF$_3$CO$_2$H].0.2 [H$_2$O]: 58.6% C; 5.7% H; Found: 58.8% C; 5.9% H.

EXAMPLE 2

Methyl 3-(2-$\alpha$-L-fucopyranosyloxy)phenyl)benzoate

Part A: 3-Bromobenzoic acid (1.1 g, 5.47 mmol) was dissolved in methanol (20 ml) in a 50 ml flask. Concentrated sulfuric acid (2 drops) was added and the mixture was refluxed under nitrogen for ten hours then concentrated under reduced pressure. The residue was mixed with dichloromethane (20 ml) and saturated sodium bicarbonate solution (10 ml). The organic material was separated, dried (MgSO$_4$) and concentrated under reduced pressure. The residue was flushed through silica gel with hexane/ethyl acetate (3:1), and concentrated which provided methyl 3-bromobenzoate (1.0 g, 85%).

Part B: Anisole (1.0 g, 9.25 mmol) was dissolved in dry THF (40 ml) in a dry 100 ml flask flushed with nitrogen and cooled to −78° C. n-Butyl lithium (5.8 ml of a 1.9M solution in hexanes, 11.1 mmol) was added then the cooling bath was exchanged for an ice-water bath. The reaction was stirred for an hour at 0° C. then trimethyl borate (1.26 ml, 10 mmol) was added and the mixture was stirred at room temperature overnight. The reaction mixture was treated with 2N aqueous HCl to pH 3 and mixed well for 30 minutes, then extracted with ether (3×15 ml). The organic materials were combined, dried (MgSO$_4$) then concentrated under reduced pressure which gave 1.32 g (87%) of 2-methoxybenzeneboronic acid as a clear oil.

Methyl 3-bromobenzoate (1.99 g, 9.25 mmol), tetrakis(triphenylphosphine) palladium(0) (110 mg), sodium carbonate (2.04 g, 19 mmol in 5 ml water) and toluene (10 ml) were degassed under nitrogen in a 25 ml flask fitted with a reflux condenser. 2-Methoxybenzeneboronic acid (1.46 g, 9.61 mmol) in toluene (1 ml) was added and the mixture was heated at reflux for two days then mixed with 1:1 saturated sodium chloride/ethyl acetate (15 ml). The organic materials were separated, dried (MgSO$_4$) then concentrated under reduced pressure. The residue was purified by flash chromatography (SiO$_2$, gradient hexane to 8:1 hexane/ethyl acetate) which gave methyl 3-(2-methoxyphenyl)benzoate (1.43 g, 64%), m.p.: 92°–93° C.

Part C: In a dry 50 ml flask, methyl 3-(2-methoxyphenyl)benzoate (1.2 g, 4.95 mmol) was dissolved in dichloromethane (10 ml) under nitrogen, and chilled in a dry-ice/2-propanol bath. Boron tribromide dimethyl sulfide complex (20 ml of a 1M solution in methylene chloride) was added slowly drop-wise and the mixture was allowed to come to room temperature, then the mixture was heated at reflux for 30 hours, then mixed with ice-water (100 ml). The organic material was separated, washed with saturated sodium bicarbonate solution (50 ml), water (50 ml), saturated sodium chloride (60 ml) then dried (MgSO$_4$) and concentrated under reduced pressure. The residue was re-esterified by treatment with methanol and catalytic sulfuric acid, and the product subsequently purified by flash chromatography (SiO$_2$, 3:1 hexane/ethyl acetate) which gave 0.95 g (84%) of methyl 3-(2-hydroxyphenyl)benzoate as a clear oil.

Part D: Operating as in Part C of EXAMPLE 1, but employing methyl 3-(2-hydroxyphenyl) benzoate gave methyl 3-(2-(2,3,4-tri-O acetyl-$\alpha$-L-fucopyranosyloxy)phenyl)benzoate in 37% yield, m.p.: 100°–105° C.

Part E: Methyl 3-(2-(2,3,4-tri-O acetyl-$\alpha$-L-fucopyranosyloxy)phenyl)benzoate (1.08 g, 1.45 mmol) was dissolved in methanol (25 ml) in a 50 ml flask, then treated with sodium methoxide (100 mg) and the mixture was stirred at room temperature overnight. The mixture was concentrated and the residue was flushed through silica gel with 7:3 methylene chloride/methanol which provided methyl 3-(2-($\alpha$-L-fucopyranosyloxy)phenyl)benzoate (0.48 g, 59%) as a white solid, m.p.: 137°–140° C.; $^1$H NMR (300 MHz, CDCl$_3$): 8.27 (s, 1H), 8.00 (d, J=8, 1H), 7.75 (d, J=8, 1H), 7.51 (t, J=8, 1H), 7.32–7.44 (comp, 3H), 7.10–7.20 (comp, 1H), 5.54 (d, J=2.7, 1H), 3.94 (s, 3H), 3.60–4.10 (comp, 7H), 1.26 (d, J=6, 3H); IR (KBr): 3421, 2938, 1718, 1437, 1245, 1083, 1035, 964, 844, 763; analysis: calculated for C$_{20}$H$_{22}$O$_7$.0.25[H$_2$O]: 63.4% C; 6.0% H. found: 63.3% C; 5.9% H.

EXAMPLE 3

3-(2-(α-L-Fucopyranosyloxy)phenyl)benzoic Acid

Methyl 3-(2-(α-L-fucopyranosyloxy)phenyl)benzoate (0.44 g, 1.18 mmol) was dissolved in acetonitrile (8 ml) and treated with a solution of lithium hydroxide hydrate (60 mg, 1.41 mM, in 0.5 ml water) and the mixture was stirred overnight at room temperature. The mixture was then treated with 2N HCl to pH 3 to 4 and the volatiles were removed under reduced pressure. The residue was purified by HPLC (reverse-phase, gradient elution 5–50% acetonitrile in water, 0.1% trifluoroacetic acid, monitored at 254 nm) which gave 3-(2-α-L-fucopyranosyloxy)phenyl)benzoic acid (174 mg, 40%) as a white solid, m.p.: 92°–93° C.; $^1$H NMR (300 MHz, DMSO-$d_6$): 8.07 (s, 1H), 7.88 (t, J=8.7, 2H), 7.51 (t, J=7.7, 1H), 7.29–7.43 (comp, 2H), 7.27 (d, J=8, 1H), 7.09 (t, J=7.2, 1H), 5.49 (d, J=3, 1H), 3.05–3.90 (comp, 7H), 0.97 (d, J=6, 3H); IR (KBr): 3402, 2932, 1695, 1498, 1457, 1219, 1076, 960, 838, 750; analysis: calculated for $C_{19}H_{20}O_7 \cdot 0.3$ [$CF_3CO_2H$] $\cdot 0.2[H_2O]$: 59.1% C; 5.2% H. found: 59.1% C; 5.5% H.

That which is claimed is:

1. A compound having the formula:

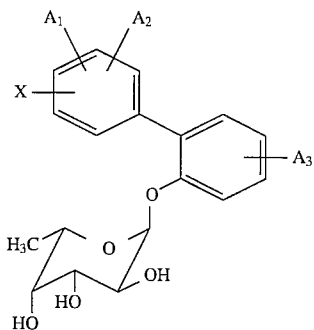

wherein X is selected from the group consisting of —$CO_2R$, —$(CH_2)_nO(CH_2)_mCO_2R$, —$(CH_2)_nCO_2R$, —$(CH_2)_nSO_3H$, —$(CH_2)_nPO_3D_1D_2$, and —OH;

$A_1$ and $A_2$ are independently selected from the group consisting of hydrogen, halogen, lower alkyl, —OR, —$(CH_2)_nNR(CH_2)_mCO_2R$, —NRR, —CN, —$N_3$, and —$NO_2$; and $A_3$ is hydrogen, halogen, lower alkyl, —$(CH_2)_pNH_2$, —$(CH_2)_pNR(CH_2)_qCO_2R$, or —$(CH_2)_pNH(CH_2)_qCH_3$;

where n and m are independently 1 to 6, p and q are independently 0 to 12, R is lower alkyl or hydrogen, and $D_1$ and $D_2$ are independently hydrogen or methyl, and the pharmaceutically acceptable salts, esters, and amides thereof.

2. A compound having the formula:

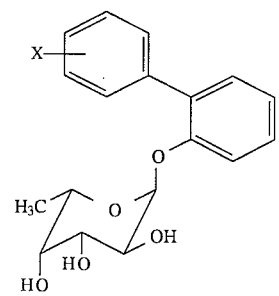

wherein X is —$CO_2R$ or —$(CH_2)_nO(CH_2)_mCO_2R$, where n and m are independently 1 to 6 inclusive and R is hydrogen or lower alkyl, and the pharmaceutically acceptable salts, esters, and amides thereof.

3. The compound of claim 2 wherein X is —$CO_2CH_3$.

4. The compound of claim 2 wherein X is —$CH_2OCH_2CO_2H$.

5. A method of inhibiting the binding of E-selectin or P-selectin to sialyl-Lewis$^x$ or sialyl-Lewis$^a$ presented on a cell surface comprising the step of administering to a patient a pharmaceutically effective amount of at least one compound having the formula:

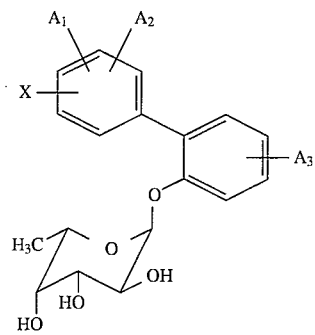

wherein X is selected from the group consisting of —$CO_2R$, —$(CH_2)_nO(CH_2)_mCO_2R$, —$(CH_2)_nCO_2R$, —$(CH_2)_nSO_3H$, —$(CH_2)_nPO_3D_1D_2$, and —OH;

$A_1$ and $A_2$ are independently selected from the group consisting of hydrogen, halogen, lower alkyl, —OR, —$(CH_2)_nNR(CH_2)_mCO_2R$, —NRR, —CN, —$N_3$, and —$NO_2$; and $A_3$ is hydrogen, halogen, lower alkyl, —$(CH_2)_pNH_2$, —$(CH_2)_pNR(CH_2)_qCO_2R$, or —$(CH_2)_pNH(CH_2)_qCH_3$;

where n and m are independently 1 to 6, p and q are independently 0 to 12, R is lower alkyl or hydrogen, and $D_1$ and $D_2$ are independently hydrogen or methyl, and the pharmaceutically acceptable salts, esters, and amides thereof.

6. A pharmaceutical composition comprising a compound of claim 1 and a pharmaceutically acceptable carrier.

* * * * *